(12) United States Patent
Kobayashi et al.

(10) Patent No.: US 11,160,552 B2
(45) Date of Patent: Nov. 2, 2021

(54) MEDICAL MANIPULATOR

(71) Applicant: OLYMPUS CORPORATION, Tokyo (JP)

(72) Inventors: Masayuki Kobayashi, Tokyo (JP); Yoshiyuki Kumada, Tokyo (JP); Keisuke Tsurimoto, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 244 days.

(21) Appl. No.: 16/272,023

(22) Filed: Feb. 11, 2019

(65) Prior Publication Data

US 2019/0167267 A1 Jun. 6, 2019

Related U.S. Application Data

(63) Continuation of application No. PCT/JP2017/017714, filed on May 10, 2017.

(30) Foreign Application Priority Data

Nov. 24, 2016 (WO) .................. PCT/JP2016/084830

(51) Int. Cl.
*A61B 17/072* (2006.01)
*A61B 17/115* (2006.01)
*A61B 17/068* (2006.01)
*A61B 17/00* (2006.01)

(52) U.S. Cl.
CPC ...... *A61B 17/07207* (2013.01); *A61B 17/068* (2013.01); *A61B 17/115* (2013.01);
(Continued)

(58) Field of Classification Search
CPC ............ A61B 17/07207; A61B 17/068; A61B 17/115
(Continued)

(56) References Cited

U.S. PATENT DOCUMENTS 4,573,622 A * 3/1986 Green .................. A61B 17/072
227/19
5,197,649 A * 3/1993 Bessler ............... A61B 17/1114
227/156
(Continued)

FOREIGN PATENT DOCUMENTS

EP 0800792 A1 10/1997
EP 1897501 A1 3/2008
(Continued)

OTHER PUBLICATIONS

International Search Report dated Jun. 13, 2017 issued in PCT/JP2017/017714.
(Continued)

*Primary Examiner* — Nathaniel C Chukwurah
(74) *Attorney, Agent, or Firm* — Scully, Scott, Murphy & Presser, P.C.

(57) ABSTRACT

A medical manipulator includes: an elongated support member; an end effector that is supported at a distal end of the support member so as to be movable in a longitudinal axial direction; a first pulling pulley that is supported so as to be rotatable about a first shaft that is secured to the end effector and that is orthogonal to the longitudinal axis; and a first wire that is wound around the first pulling pulley so as to cause, when a proximal end thereof is pulled, tensile forces in substantially the same directions to act on the first pulling pulley on either side of the first pulling pulley flanking the first shaft.

16 Claims, 8 Drawing Sheets

(52) U.S. Cl.
CPC . *A61B 17/1155* (2013.01); *A61B 2017/00398* (2013.01); *A61B 2017/07257* (2013.01); *A61B 2017/07271* (2013.01); *A61B 2017/07285* (2013.01)

(58) Field of Classification Search
USPC ...................................................... 227/175.1
See application file for complete search history.

(56) References Cited

U.S. PATENT DOCUMENTS

| | | | |
|---|---|---|---|
| 5,507,773 | A | 4/1996 | Huitema et al. |
| 7,278,563 | B1 * | 10/2007 | Green .............. A61B 17/07207 227/176.1 |
| 2003/0218047 | A1 | 11/2003 | Sharma et al. |
| 2004/0118896 | A1 | 6/2004 | Sharma et al. |
| 2005/0263561 | A1 | 12/2005 | Sharma et al. |
| 2008/0308601 | A1 | 12/2008 | Timm et al. |
| 2009/0112229 | A1 | 4/2009 | Omori et al. |
| 2009/0277948 | A1 | 11/2009 | Beardsley et al. |
| 2010/0038403 | A1 | 2/2010 | D'Arcangelo |
| 2015/0157318 | A1 | 6/2015 | Beardsley et al. |
| 2016/0317172 | A1 | 11/2016 | Kumada et al. |

FOREIGN PATENT DOCUMENTS

| | | | |
|---|---|---|---|
| EP | 2005896 A2 | A2 | 12/2008 |
| EP | 2116197 | A2 | 11/2009 |
| JP | H08-033628 | A | 2/1996 |
| JP | H11-253389 | A | 9/1999 |
| JP | H11-253390 | A | 9/1999 |
| JP | 2002-136467 | A | 5/2002 |
| JP | 2005-526568 | A | 9/2005 |
| JP | 2009-034487 | A | 2/2009 |
| JP | 2009-106606 | A | 5/2009 |
| JP | 2009-268910 | A | 11/2009 |
| JP | 2010-502324 | A | 1/2010 |
| JP | 2015-093033 | A | 5/2015 |
| JP | 2015-173729 | A | 10/2015 |
| WO | WO 03/099138 | A2 | 12/2003 |
| WO | WO 2008/028700 | A1 | 3/2008 |
| WO | WO 2009/057347 | A1 | 5/2009 |
| WO | WO 2015/137181 | A1 | 9/2015 |

OTHER PUBLICATIONS

International Search Report dated Jan. 31, 2017 issued in PCT/JP2016/084830.

* cited by examiner

MEDICAL MANIPULATOR

CROSS-REFERENCE TO RELATED APPLICATIONS

This is a continuation of International Application PCT/JP2017/017714 which is hereby incorporated by reference herein in its entirety.

This application claims the benefit of International Application PCT/JP2016/084830, the content of which is incorporated herein by reference.

TECHNICAL FIELD

The present invention relates to a medical manipulator.

BACKGROUND ART

As a treatment tool that simultaneously sutures and cuts tissue, there is a known medical manipulator such as a medical stapler (for example, see Patent Literature 1).

This medical stapler is provided with, inside a pair of jaws that grip pieces of tissue, numerous staples, a mechanism for ejecting the staples, an anvil that deforms the ejected staples, and a cutter that cuts the pieces of tissue that have been joined with the staples.

CITATION LIST

Patent Literature

{PTL 1} Japanese Translation of PCT International Application, Publication No. 2010-502324

SUMMARY OF INVENTION

An aspect of the present invention is a medical manipulator including: an elongated support member; an end effector that is supported at a distal end of the support member so as to be movable in a longitudinal axial direction; a first pulling pulley that is supported so as to be rotatable about a first shaft that is secured to the end effector and that is orthogonal to the longitudinal axis; and; a first wire that is wound around the first pulling pulley so as to cause, when a proximal end thereof is pulled, tensile forces in substantially the same directions to act on the first pulling pulley on either side of the first pulling pulley flanking the first shaft.

DESCRIPTION OF EMBODIMENT

A medical manipulator 1 according to an embodiment of the present invention will be described below with reference to the drawings.

Figure 1:
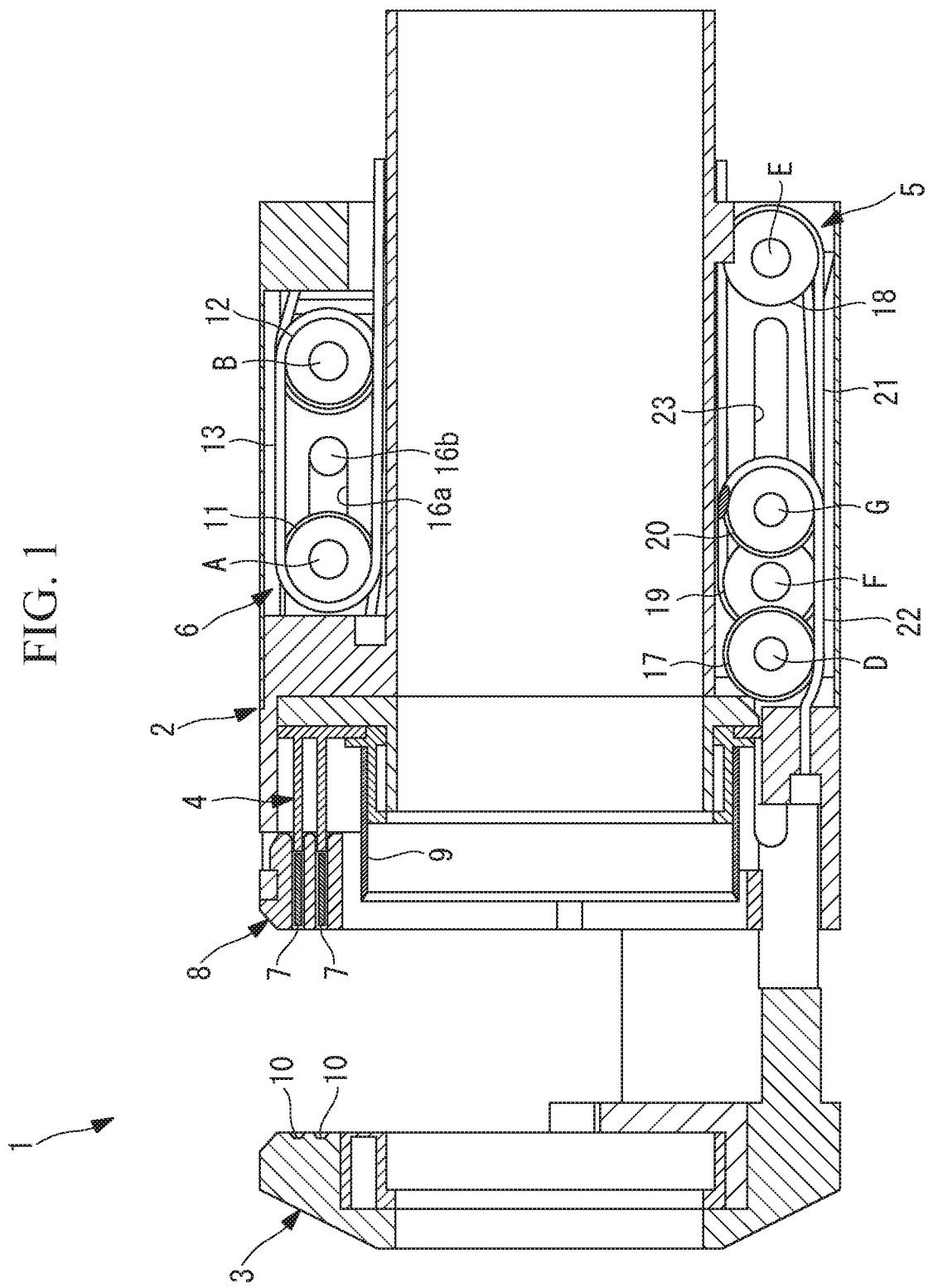
FIG. 1 is a partial longitudinal cross-sectional view showing a medical manipulator according to an embodiment of the present invention.

As shown in FIG. 1, the medical manipulator 1 according to this embodiment is a medical stapler (hereinafter also referred to as medical stapler 1) provided with: an elongated tubular support member 2; an anvil 3; a pusher (end effector, pushing member) 4; an anvil-driving mechanism 5; and a pusher-driving mechanism 6. The anvil 3 is supported at a distal end of the support member 2 so as to be movable along a longitudinal axis of the support member 2. The pusher 4 is disposed facing the anvil 3 and is similarly supported at the distal end of the support member 2 so as to be movable along the longitudinal axial direction thereof. The anvil-driving mechanism 5 moves the anvil 3. The pusher-driving mechanism 6 moves the pusher 4.

A cassette 8 that accommodates numerous staples 7 is disposed on the distal-end side of the pusher 4. In addition, the pusher 4 supports the cutter 9; as a result of the pusher 4 being pushed out toward the distal end in the longitudinal axial direction by the pusher-driving mechanism 6, the plurality of staples 7 accommodated in the cassette 8 are pushed out all at once, thus joining pieces of tissue together; and the joined pieces of tissue are cut by the cutter 9.

The anvil 3 is provided with, at positions that face the individual staples 7 supported by the cassette 8, a plurality of depressions 10 that receive and deform the staples 7 pushed out by the pusher 4. As a result of the anvil-driving mechanism 5 applying, to the anvil 3, a force that acts toward the proximal end in the longitudinal axial direction, the anvil 3 receives the force from the pusher 4 and deforms the staples 7 between the pusher 4 and the anvil 3.

Figure 2:
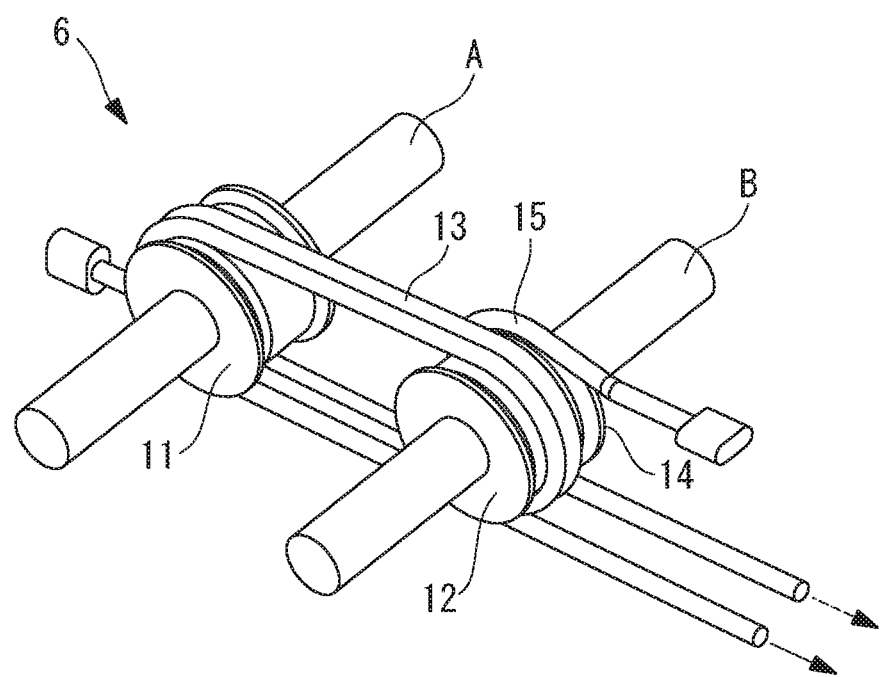
FIG. 2 is a perspective view for explaining a pusher-driving mechanism of the medical manipulator in FIG. 1.

As shown in FIGS. 1 and 2, the pusher-driving mechanism 6 is provided with: a fixed pulley 11 that is supported so as to be rotatable about a fixed shaft A that is secured to the distal end of the support member 2 and that extends in an orthogonal direction with respect to the longitudinal axis; a movable pulley (first pulling pulley) 12 that is supported so as to be rotatable about a movable shaft (first shaft) B that is secured to the pusher 4 and that is disposed parallel to and away from the fixed shaft A so as to be closer to the proximal end than the fixed shaft A is; and a pushing wire (first wire) 13 that is wound around the fixed pulley 11 and the movable pulley 12.

The pushing wire 13 is secured to the support member 2 at a distal end thereof, extends toward the proximal end in the longitudinal axial direction of the support member 2 after being wound twice between the movable pulley 12 and the fixed pulley 11, is pulled out to the exterior of the support member 2 from the proximal end of the support member 2, and is connected to a manipulator (not shown). The manipulator is manipulated by an operator and applies a pulling force that pulls the pushing wire 13 toward the proximal end.

As shown in FIG. 2, the movable shaft B supports a pulling pulley 14 in a rotatable manner, and a pulling wire 15 is wound around the pulling pulley 14. The pulling wire 15 is secured to the support member 2 at a distal end thereof, extends in the longitudinal axial direction of the support member 2 after being wound around the pulling pulley 14, is pulled out to the exterior of the support member 2 from the proximal end of the support member 2, and is connected to the manipulator (not shown).

Figure 3:
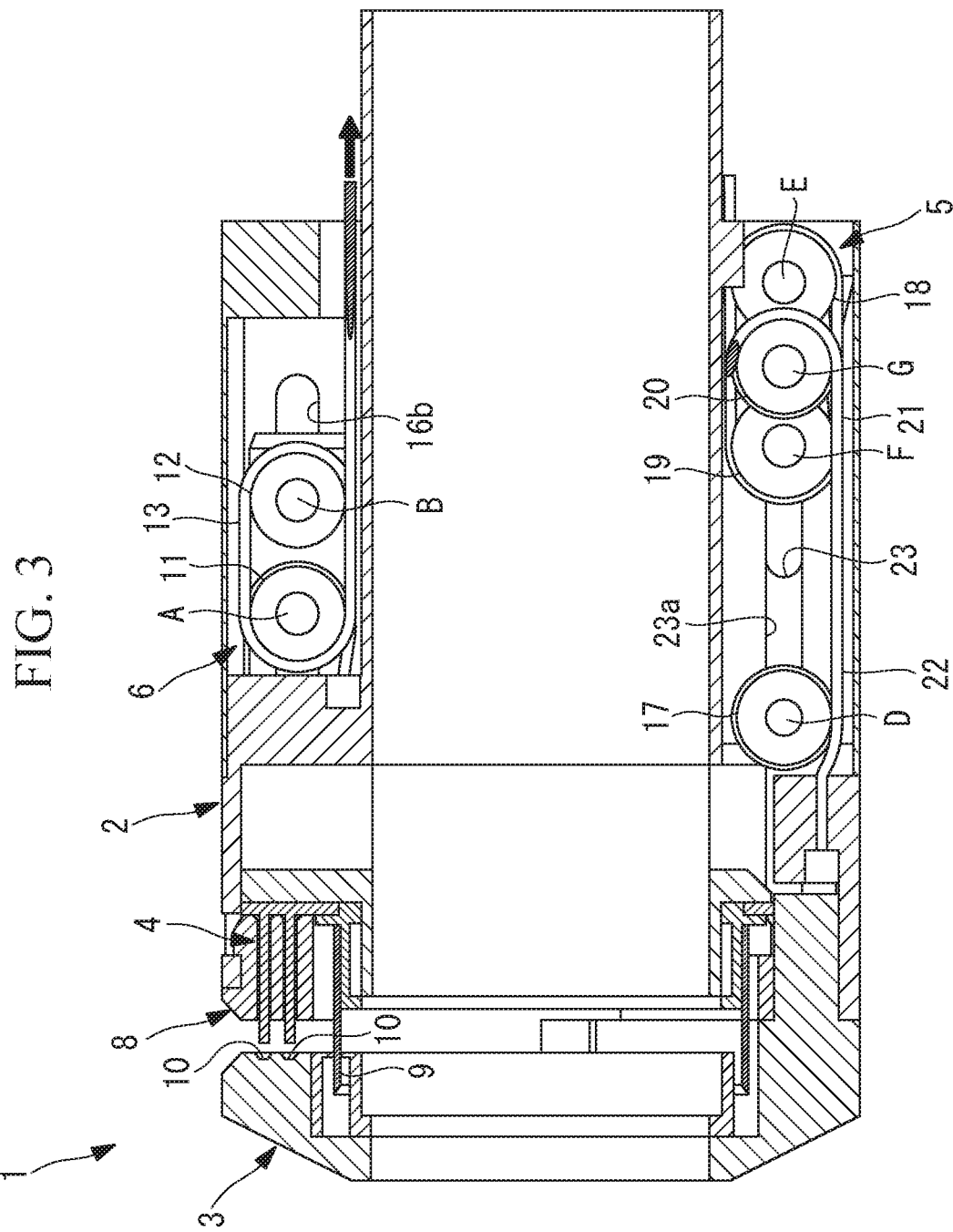
FIG. 3 is a longitudinal cross-sectional view showing a state in which a pusher is pushed out by the pusher-driving mechanism in FIG. 2.

As shown in FIG. 1, the pusher 4 is provided with a slit 16a that extends in the longitudinal axial direction, and that makes an axle A of the fixed pulley 11 pass therethrough. In addition, as shown in FIG. 3, the support member 2 is provided with a slit 16b that extends in the longitudinal axial direction and that causes an axle B of the movable pulley 12 to be disposed in an inserted state.

Figure 4:
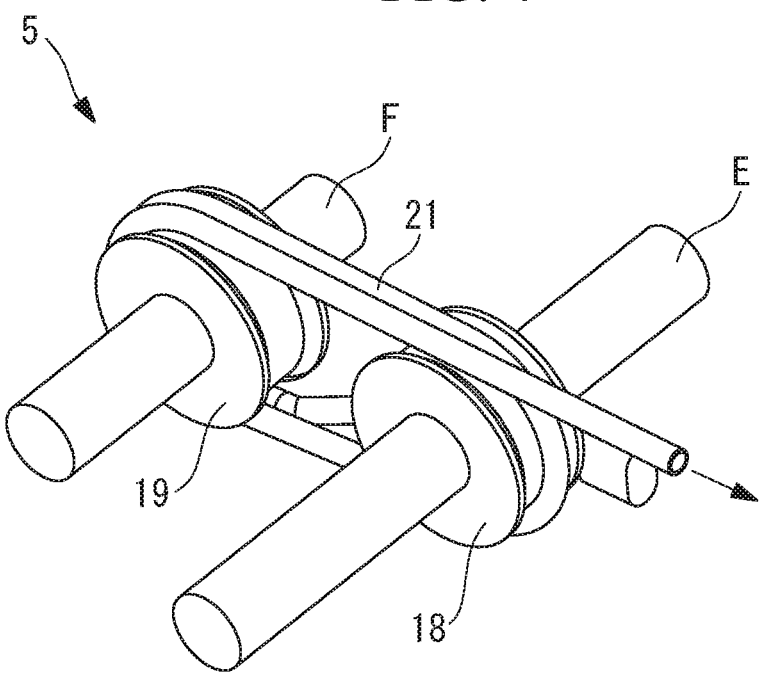
FIG. 4 is a perspective view for explaining a portion of an anvil-driving mechanism of the medical manipulator in FIG. 1.
Figure 5:
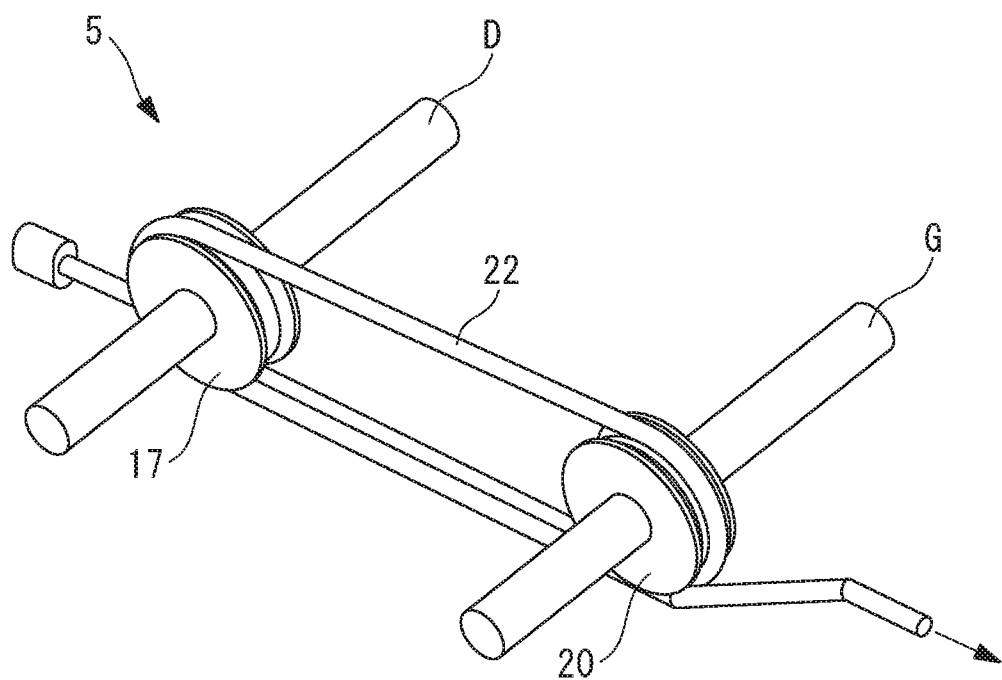
FIG. 5 is a perspective view for explaining another portion of the anvil-driving mechanism in FIG. 4.

As shown in FIGS. 1, 4, and 5, the anvil-driving mechanism 5 is provided with: two fixed pulleys 17 and 18; two movable pulleys (second pulling pulleys) 19 and 20; a pulling wire (second wire) 21; and a pushing wire (anvil pulling means) 22. The two fixed pulleys 17 and 18 are secured to the distal end of the support member 2 with a spacing therebetween in the longitudinal axial direction and are supported so as to be individually rotatable about two fixed shafts D and E extending in the orthogonal direction with respect to the longitudinal axis. The two movable pulleys 19 and 20 are disposed parallel to and away from the fixed shafts D and E between the two fixed shafts D and E and are supported so as to be rotatable about two parallel movable shafts (second shafts) F and G secured to the anvil 3. The pulling wire 21 and pushing wire 22 are wound around the fixed pulleys 17 and 18 and the movable pulleys 19 and 20.

As shown in FIG. 4, the pulling wire 21 is secured to the support member 2 at a distal end thereof, extends toward the proximal end in the longitudinal axial direction of the support member 2 after being wound twice between the movable pulley 19 and the fixed pulley 18 on the proximal-end side, is pulled out to the exterior of the support member 2 from the proximal end of the support member 2, and is connected to the manipulator (not shown).

As shown in FIG. 5, the pushing wire 22 is secured to the support member 2 at a distal end thereof, is folded back by the fixed pulley 17 on the distal-end side after being wound once around the movable pulley 20, extends toward the proximal end in the longitudinal axial direction of the support member 2, is pulled out to the exterior of the support member 2 from the proximal end of the support member 2, and is connected to the manipulator (not shown).

As shown in FIG. 3, the anvil 3 is also provided with a slit 23a that extends along the longitudinal axial direction and that makes an axle D of the fixed pulley 17 on the distal-end side pass therethrough. In addition, as shown in FIG. 1, the support member 2 is provided with a slit 23 that extends along the longitudinal axial direction and that causes at least one of an axle F of the movable pulley 19 and an axle G of the movable pulley 20 to be disposed in an inserted state.

The operation of the thus-configured medical stapler 1 according to this embodiment will be described below.

In order to join pieces of tissue in the body of a patient by using the medical stapler 1 according to this embodiment, a distal-end portion of the medical stapler 1 is disposed inside the body, and, in the state in which a distal-end surface of the cassette 8 and the anvil 3 are separated in the longitudinal axial direction, as shown in FIG. 1, the pieces of tissue to be joined are inserted between the cassette 8 and the anvil 3. The manipulator is manipulated in this state, and a pulling force with which the pulling wire 21 provided in the anvil-driving mechanism 5 is pulled toward the proximal end is applied. Note that the pulling wire 21 may be manually pulled via the manipulation of the manipulator, or the pulling wire 21 may be electrically pulled by actuating a motor via the manipulation of the manipulator.

Figure 6:
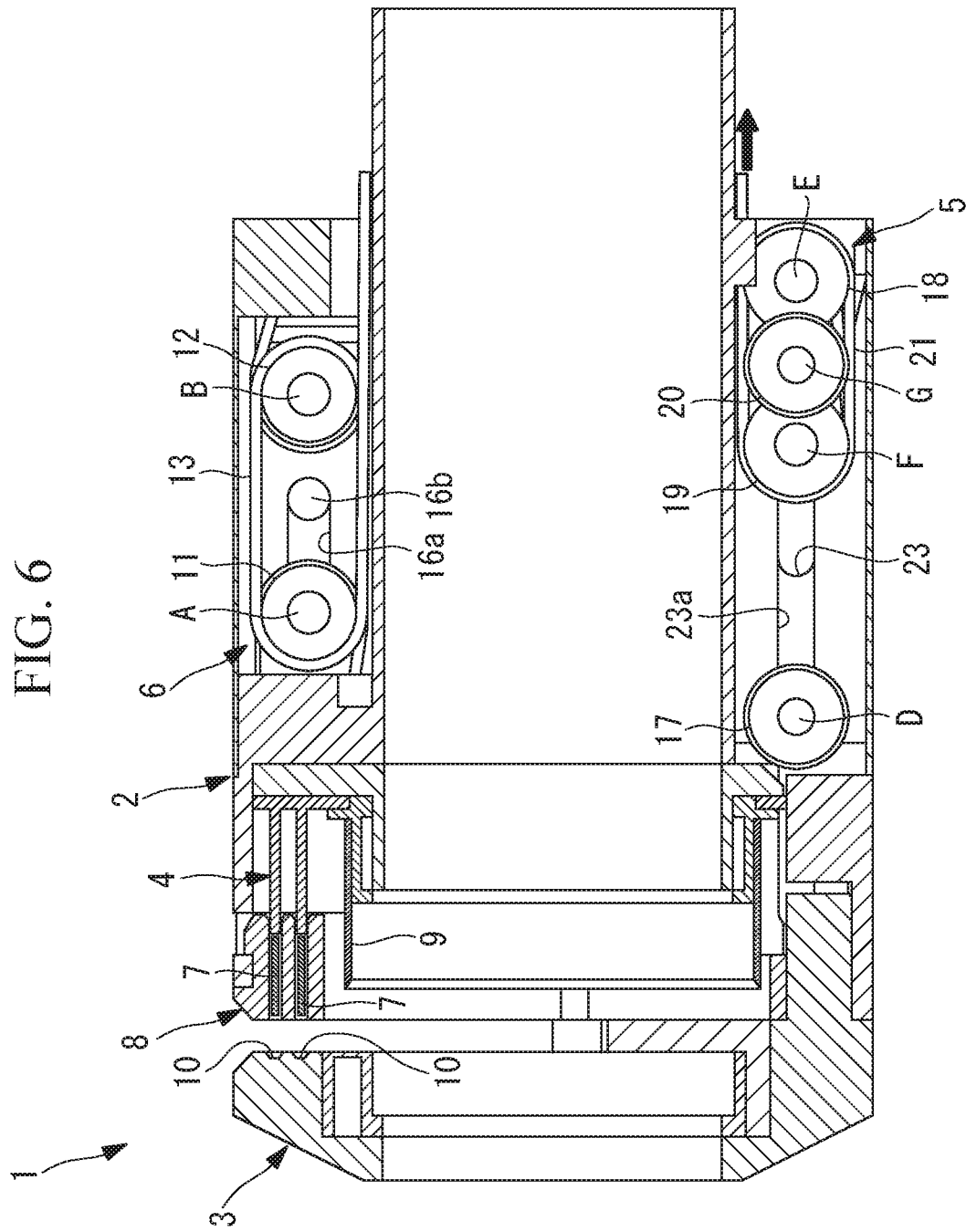
FIG. 6 is a longitudinal cross-sectional view showing a state in which an anvil is pulled toward a proximal end by the anvil-driving mechanism in FIG. 3.

As shown in FIG. 6, as a result of the pulling wire 21 being pulled, a tensile force generated in the pulling wire 21 acts on either side of the movable shaft F of the movable pulley 19, and the movable pulley 19 is pulled toward the proximal end, serving as a movable pulley. Because the pulling wire 21 is wound twice between the movable pulley 19 and the fixed pulley 18, tensile forces generated in two wires on each side of the movable pulley 19, that is, a total of four pulling wires 21, act on the movable pulley 19 in substantially the same direction so as to pull the movable pulley 19 toward the proximal end. By doing so, the anvil 3, to which the movable shaft F of the movable pulley 19 is secured, is pulled toward the proximal end by a pulling force that is four times the amount of the manipulating force applied by means of the manipulator, and the pieces of tissue are clamped between the anvil 3 and the distal-end surface of the cassette 8.

Next, as shown in FIG. 3, the manipulator is manipulated, and the pushing wire 13 provided in the pusher-driving mechanism 6 is pulled toward the proximal end. As a result of the pushing wire 13 being pulled, the tensile force generated in the pushing wire 13 acts on either side of the movable shaft B of the movable pulley 12, and the movable pulley 12 is pulled toward the distal end. Because the pushing wire 13 is wound twice between the movable pulley 12 and the fixed pulley 11, tensile forces generated in two wires on each side of the movable pulley 12, that is, a total of four pushing wires 13, act on the movable pulley 12 in substantially the same direction so as to push out the movable pulley 12 toward the distal end.

By doing so, the pusher 4, to which the movable shaft B of the movable pulley 12 is secured, is pushed out toward the distal end by a pushing force that is four times the amount of the manipulating force applied by means of the manipulator, and the plurality of staples 7 supported by the pusher 4 are pushed out all at once toward the distal end.

The individual staples 7 pushed out by the pusher 4 pass through the pieces of tissue in the longitudinal axial direction with sharp tips thereof, and join the pieces of tissue by being deformed by the depressions 10 provided in the anvil 3.

In addition, as a result of the cutter 9 provided in the pusher 4 being pushed out toward the distal end in the longitudinal axial direction, the joined pieces of tissue are cut by the cutter 9, and thus, the treatment is completed.

In this case, with the medical stapler 1 according to this embodiment, the amount of the manipulating force applied to the pushing wire 13 is amplified four fold by the pusher-driving mechanism 6, and, with this force, the plurality of staples 7 are pushed and the cutter 9 cuts the pieces of tissue; therefore, it suffices to apply only a small amount of manipulating force. As a result, there is an advantage in that it is possible to considerably reduce the burden on the operator.

In particular, in the case where the support member 2 is a tube-like member formed of an elongated and flexible material, if the support member 2 is bent in a route before reaching a target site, friction between the support member 2 and the wires 13, 15, 21, and 22 at the interior thereof increases, and it is necessary to apply a large amount of manipulating force; however, with this embodiment, there is an advantage in that it is possible to more reliably push out the pusher 4 with the force amplified by the pusher-driving mechanism 6 even if the tensile force is attenuated by the friction.

In addition, in this embodiment, because the anvil 3 is pulled toward the proximal end by the force that has been amplified by the anvil-driving mechanism 5 to four times the amount of the manipulating force applied to the pulling wire 21, it is possible to receive the forces of the plurality of staples 7 pushed out by the pusher 4 with a large force and cutter 9. In particular, because, as a result of making the number of windings of the pulling wire 21 and that of the pushing wire 13 the same, the amplification factor of the force with which the anvil 3 is pulled toward the proximal end is set to be equal to the amplification factor of the force with which the pusher 4 is pushed toward the distal end, and the forces of the plurality of staples 7 pushed out by the pusher 4 with a large force and cutter 9 are more reliably received by the anvil 3, thus making it possible to more reliably perform joining and cutting of the pieces of tissue.

Note that, in this embodiment, because the pulling pulley 14 is secured to the movable pulley 12 of the pusher-driving mechanism 6, it is possible to pull back the pusher 4 toward the proximal end by pulling the pulling wire (fourth wire) 15 wound around the pulling pulley 14 toward the proximal end.

In addition, it is possible to push out the anvil 3 toward the distal end by pulling the pushing wire (third wire) 22 wound around the fixed pulley 17 on the distal-end side of the anvil-driving mechanism 5 and the movable pulley 20, and thus, it is possible to increase the spacing between the anvil 3 and the pusher 4.

Regarding pulling back the pusher 4 toward the proximal end by means of the pusher-driving mechanism 6 and pushing out the anvil 3 toward the distal end by means of the anvil-driving mechanism 5, because the required amount of the manipulating force is not as large as that in the case of movement in the opposite direction, there is no need to amplify the force; however, it is preferable that a mechanism to amplify the force be provided, because the amount of manipulating force is reduced and it is possible to reliably achieve actuation even if there is attenuation due to friction.

In addition, a manipulating portion (anvil manipulator, pushing-member manipulator) 50 will be described, which manipulates pushing of the pusher 4 toward the distal end by means of the pusher-driving mechanism (pushing-member pulling means) 6 and pulling thereof back toward the proximal end or pushing of the anvil 3 toward the distal end by means of the anvil-driving mechanism 5 and pulling thereof back toward the proximal end.

As has been described above, the pusher-driving mechanism 6 pushes the pusher 4 toward the distal end by pulling, toward the proximal end, the pushing wire 13, which is wound around the movable pulley 12 twice, and pulls back the pusher 4 toward the proximal end by pulling, toward the proximal end, the pulling wire 15, which is wound around the pulling pulley 14 once.

Specifically, in order to push out the pusher 4 toward the distal end, it is necessary to pull the pushing wire 13 by a distance that is two times the length of the pulling wire 15 as compared with when pulling back the pusher 4 toward the proximal end. Because of this, as shown in FIG. 9, as the manipulating portion (pushing-member manipulator) 50, a two-stage pulley 51 in which two pulleys (winding portions) 51*a* and 51*b* that are concentrically secured and that have diameters that differ from each other by a factor of two may be provided, and the pushing wire 13, which needs to be pulled farther, may be wound around the pulley 51*b* having a large diameter, and the pulling wire 15 may be wound around the pulley 51*a* having a small diameter.

Figure 9:
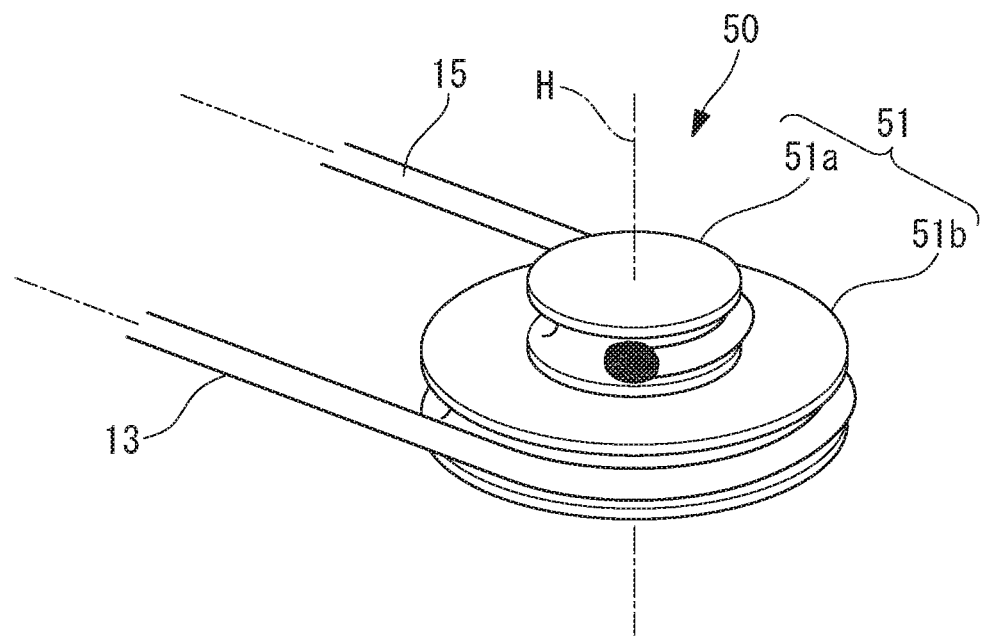
FIG. 9 is a perspective view showing an example of a manipulating portion that is connected to two wires of the pusher-driving mechanism in FIG. 2.

In addition, in the example in FIG. 9, although a case in which, in order to push out the pusher 4 toward the distal end, the pushing wire 13 is pulled by a distance that is two times the length of the pulling wire 15 as compared with when pulling back the pusher 4 toward the proximal end has been described as an example, it is not limited thereto. The ratio of the distances by which the pushing wire 13 and the pulling wire 15 are pulled with respect to the amount by which the pusher 4 is moved may be set to be equal to the ratio of the diameters of the individual pulleys 51*a* and 51*b* of the two-stage pulley 51.

As shown in FIG. 9, in the case in which the two-stage pulley 51 is employed, by winding, individually in opposite directions, the pushing wire 13 and the pulling wire 15 around the pulleys 51*a* and 51*b* having different diameters, it is possible to pull the pushing wire 13 when the two-stage pulley 51 is rotated about a rotation shaft H in one direction, and it is possible to pull the pulling wire 15 when the two-stage pulley 51 is rotated in the opposite direction. By doing so, the pulleys 51*a* and 51*b* are rotated in synchronization at circumferential speeds where the ratio thereof is equal to the ratio of the distances by which the pushing wire 13 and the pulling wire 15 are pulled with respect to the amount by which the anvil 3 is moved, and it is possible to enhance the operability by preventing the pulling wire 15, which is let out from the pulley 51*a* when pulling the pushing wire 13, from slackening.

Figure 10:
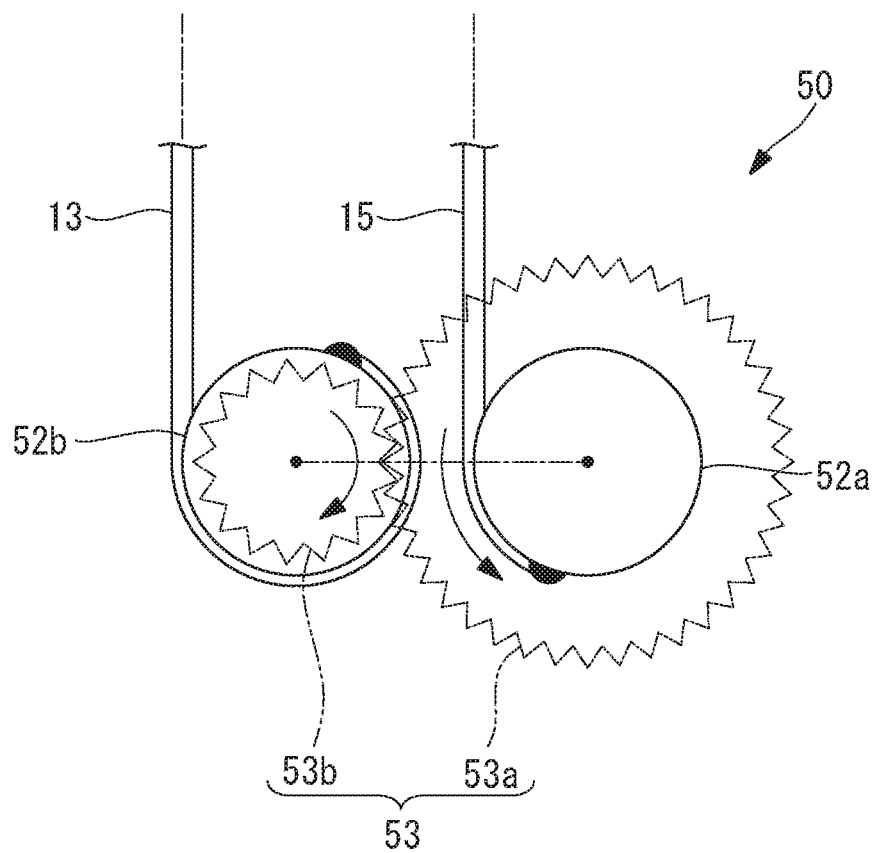
FIG. 10 is a diagram showing another example of the manipulating portion in FIG. 9.

In addition, as shown in FIG. 10, instead of employing the two-stage pulley 51, by joining two pulleys (winding portions) 52*a* and 52*b*, which have diameters that are equivalent to each other, by means of a speed-reducing mechanism 53 such as gears 53*a* and 53*b*, the circumferential speed of the pulley 52*b* may be set to be two times the circumferential speed of the pulley 52*a*. In other words, by winding the pushing wire 13 around the pulley 52*b* having a greater circumferential speed and winding the pulling wire 15 around the pulley 52*a* having a lower circumferential speed, it is possible to enhance the operability by preventing the pulling wire 15, which is let out from the pulley 52*a* when pulling the pushing wire 13, from slackening.

In addition, although the manipulating portion 50 for the pusher-driving mechanism 6 has been described as an example, it is also possible to apply a similar manipulating portion (anvil manipulator) to the anvil-driving mechanism 5.

In this case, the pulling wire 21 and the pushing wire 22 may be wound around the individual pulleys 51*a* and 51*b* of the two-stage pulley 51.

In addition, although, in the above description, the pushing wire 13 and the pulling wire 15 have been described assuming that these wires do not stretch, in reality, stretching of the pushing wire 13 and pulling wire 15 increases with an increase in the distances by which the wires are pulled; and therefore, the diameters of the pulleys 51*a*, 51*b*, 52*a*, and 52*b* or the speed reduction rate of the speed-reducing mechanism 53 may be determined in consideration of this stretching amount.

In addition, in this embodiment, the winding number of the pulling wire 21, which is wound around the movable pulley 19 of the anvil 3, is set to be equal to the winding number of the pushing wire 13, which is wound around the movable pulley 12 of the pusher 4, thus setting the amplification factors thereof to be equal to each other; however, the winding number on the anvil—3 side may be increased, thus increasing the amplification factor thereof. In addition, instead of adjusting the amplification factors by means of the winding number, multiple sets of the movable pulley 19 and the pulling wire 21 and multiple sets of the movable pulley 20 and the pushing wire 22 may be employed. Because the efficiency decreases with an increase in the winding number of the wires 21 and 22 to be wound around the movable pulleys 19 and 20, it is preferable that the forces for the movable pulleys 19 and 20 be separately amplified.

Figure 7:
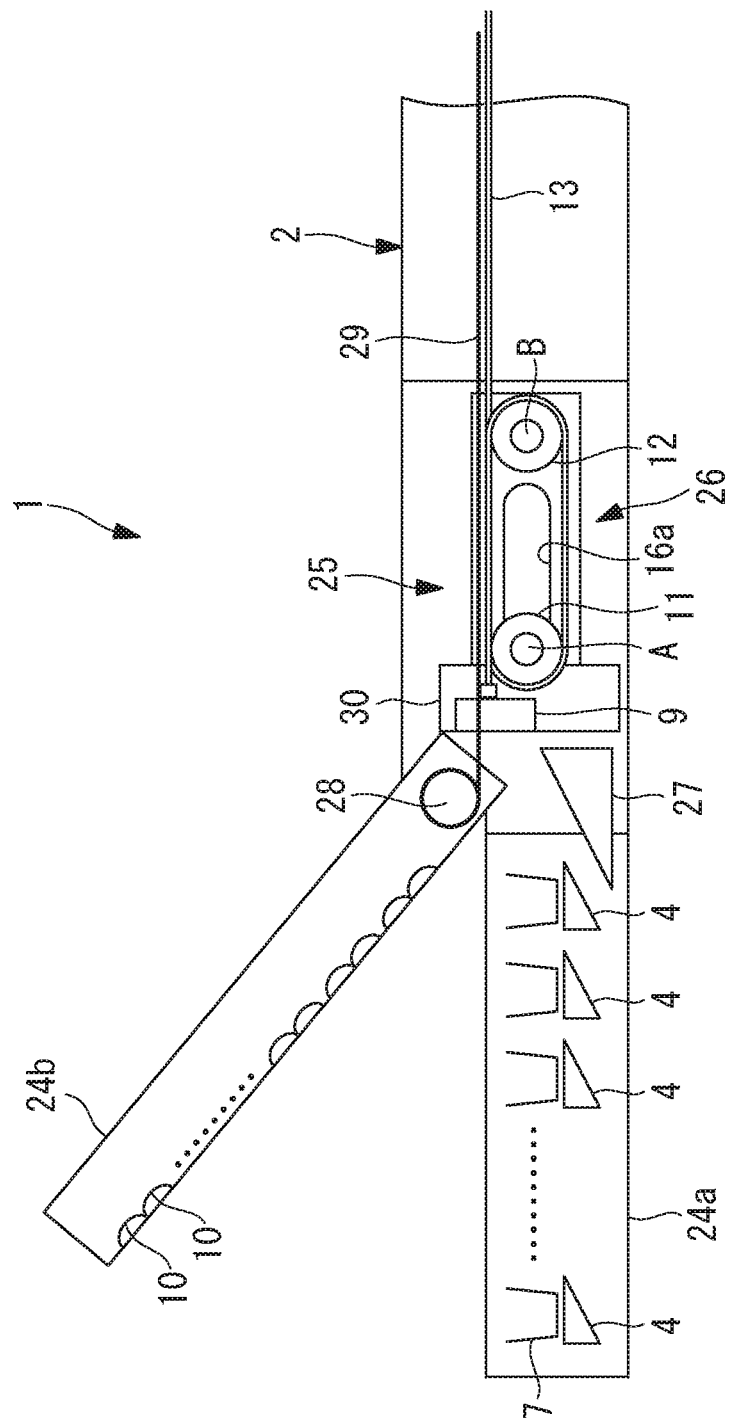
FIG. 7 is a partial schematic view showing a linear stapler, which is a first modification of the medical manipulator in FIG. 1.

In addition, although this embodiment has been described in terms of the example in which a medical stapler such as a circular stapler is employed as the medical manipulator 1, alternatively, a medical stapler such as a liner stapler may be employed, as shown in FIG. 7.

In this case, the medical manipulator 1 is provided with: the support member 2; a lower jaw (cassette) 24a; an upper jaw (anvil) 24b; a jaw driving mechanism (anvil-driving mechanism) 25; the pusher 4; a pusher-driving mechanism 26; and a slider 27. The lower jaw 24a is provided at the distal end of the support member 2 along the longitudinal axis of the support member 2. The upper jaw 24b is supported at the distal end of the support member 2 in a pivotable manner. The jaw driving mechanism 25 pivots the upper jaw 24b. The pusher-driving mechanism 26 moves the pusher 4. The slider 27 has an inclined surface that transmits the force from the pusher-driving mechanism 26 to the pusher 4.

The jaw driving mechanism 25 is provided with: a fixed pulley 28 that is secured to the upper jaw 24b and that is rotatable with respect to the support member 2; and a pulling wire (second wire) 29 in which one end thereof is secured to the fixed pulley 28.

The pulling wire 29 extends in the longitudinal axial direction of the support member 2 after being wound around the fixed pulley 28 to which the one end of the pulling wire 29 is secured, is pulled out to the exterior of the support member 2 from the proximal end of the support member 2, and is connected to a manipulator (not shown).

The pusher-driving mechanism 26 is provided with: the fixed pulley 11; the movable pulley 12; the pushing wire 13; and a driving member 30 that is moved in a direction along the longitudinal axis of the support member 2 when the movable pulley 12 is moved.

In order to join pieces of tissue inside the body of a patient, the pieces of tissue to be joined are inserted between the lower jaw 24a and the upper jaw 24b, the pulling wire 29 provided in the jaw driving mechanism 25 is pulled toward the proximal end by manipulating the manipulator in this state. As a result of the pulling wire 29 being pulled, a tensile force generated in the pulling wire 29 is transmitted to the fixed pulley 28, and the fixed pulley 28 is rotated. Due to the rotation of the fixed pulley 28, the upper jaw 24b is pivoted and brought close to the lower jaw 24a, and the pieces of tissue are clamped between the lower jaw 24a and the upper jaw 24b.

Next, the manipulator is manipulated and the pushing wire 13 provided in the pusher-driving mechanism 26 is pulled toward the proximal end, consequently pulling the movable pulley 12 toward the distal end. As a result of the movable pulley 12 being pulled toward the distal end, the driving member 30 is also pulled toward the distal end. As a result of the driving member 30, which has been pulled toward the distal end, acting so as to push out the slider 27 toward the distal end, the pusher 4 is pushed out toward the distal end by the inclined surface of the slider 27, which causes the staples 7 to be pushed out toward the upper jaw 24b from openings (not shown) in a surface of the lower jaw 24a, and the pieces of tissue are joined by the staples 7.

Figure 8:
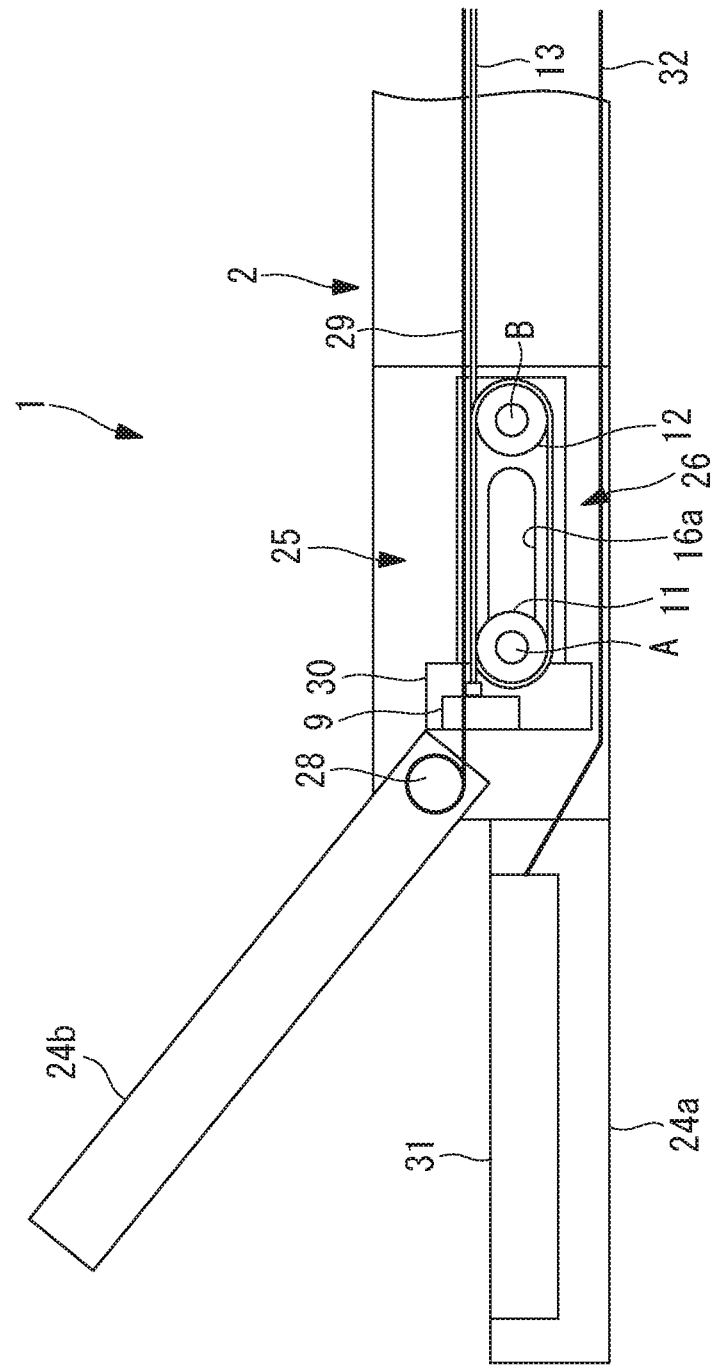
FIG. 8 is a partial schematic view showing an energy treatment tool, which is a second modification of the medical manipulator in FIG. 1

In addition, as a result of the cutter 9 provided in the driving member 30 being pushed out toward the distal end in the longitudinal axial direction, the joined pieces of tissue are cut by the cutter 9, and thus, the treatment is completed In addition, in this embodiment, as shown in FIG. 8, an energy treatment tool may be employed as the medical manipulator 1 instead of the medical stapler. In the figure, reference sign 31 is an energy portion that is capable of sealing tissue such as a blood vessel by means of energy, and reference sign 32 is an energy-transmitting portion that transmits the energy to the energy portion 31.

The above-described embodiment leads to the following invention.

An aspect of the present invention is a medical manipulator including: an elongated support member; an end effector that is supported at a distal end of the support member so as to be movable in a longitudinal axial direction; a first pulling pulley that is supported so as to be rotatable about a first shaft that is secured to the end effector and that is orthogonal to the longitudinal axis; and; a first wire that is wound around the first pulling pulley so as to cause, when a proximal end thereof is pulled, tensile forces in substantially the same directions to act on the first pulling pulley on either side of the first pulling pulley flanking the first shaft.

With this aspect, when the distal end of the elongated support member is disposed in the vicinity of a target site and a force is applied so as to pull the proximal end of the first wire toward the proximal end, the tensile force is transmitted by the first wire and the tensile force acts, in substantially the same direction, on either side of the first shaft of the first pulling pulley. By doing so, a force that is substantially two times the tensile force acts on the first shaft of the first pulling pulley, and the end effector to which the first shaft of the first pulling pulley is secured is moved in longitudinal axial direction at the distal end of the support member. By doing so, it is possible to move the end effector at the distal end of the support member with the force that is substantially two times the applied force, and it is possible to reduce the amount of manipulating force required to actuate the end effector.

In the above-described aspect, the support member may include a slit that supports an axle of the first pulling pulley so as to allow movement thereof in a longitudinal axial direction.

By doing so, as a result of generating the tensile force in the first wire, the axle of the first pulling pulley is guided by the slit provided in the support member, and the first pulling pulley is moved in the longitudinal axial direction of the support member.

In addition, the above-described aspect may be provided with two or more sets of the first pulling pulley and the first wire.

By doing so, with the first wires and the first pulling pulleys of the individual sets, it is possible to individually amplify the forces applied to the first wires substantially two fold, and it is possible to actuate the end effector with a smaller amount of manipulating force.

In addition, in the above-described aspect, the end effector may be a pushing member that pushes out a staple By doing so, the manipulating force applied to the proximal end of the first wire is transmitted to the pushing member, which constitutes the end effector, after the amount thereof is amplified, and it is possible to push out the staple with a large force. By doing so, it is possible to reduce the amount of the manipulating force required when joining pieces of tissue with the staple.

In addition, the above-described aspect may be provided with: an anvil that is supported at the distal end of the support member so as to be movable in the longitudinal axial direction and that deforms the staple that is pushed out by the pushing member toward the distal end in the longitudinal axial direction; a second pulling pulley that is supported so as to be rotatable about a second shaft that is secured to the anvil and that is orthogonal to the longitudinal axis; and a second wire that is wound around the second pulling pulley so as to cause, when a proximal end thereof is pulled, tensile forces applied toward the proximal end in the longitudinal axial direction on either side of the second pulling pulley flanking the second shaft to act on the second pulling pulley.

By doing so, as a result of pulling the proximal end of the second wire toward the proximal end, the tensile force acts on either side of the second shaft of the second pulling pulley around which the second wire is wound, and the anvil to which the second shaft of the second pulling pulley is secured is pulled toward the proximal end. Meanwhile, as described above, as a result of pulling the proximal end of the first wire toward the proximal end, the tensile force acts on either side of the first shaft of the first pulling pulley around which the first wire is wound, and the pushing member to which the first shaft of the first pulling pulley is secured is pushed out toward the distal end, thereby pushing out the staple toward the distal end.

As a result of disposing pieces of tissue to be joined between the pushing member and the anvil and actuating the anvil and the pushing member, it is possible to join the pieces of tissue by deforming the staple that has passed therethrough by means of the anvil.

In this case, because the forces applied to the pushing member and the anvil both are amplified by the combination of the wires and the pulling pulleys, it is possible to join the pieces of tissue with a small amount of the manipulating force.

In addition, the above-described aspect may be provided with two or more sets of the second pulling pulley and the second wire.

By doing so, with the second wires and the second pulling pulleys of the individual sets, it is possible to individually amplify the forces applied to the second wires substantially two fold, and it is possible to pull the anvil with a smaller amount of manipulating force.

In addition, in the above-described aspect, a force that causes the anvil to be moved toward the proximal end in the longitudinal axial direction as a result of the second wire being pulled may be equal to or greater than a force that causes the pushing member to be moved toward the distal end in the longitudinal axial direction as a result of the first wire being pulled.

By doing so, it is possible to stably receive the force from the pushing member with the anvil, and it is possible to perform stable joining by means of the staple.

In addition, in the above-described aspect, the number of times the second wire is wound around the second pulling pulley may be equal to or greater than the number of times the first wire is wound around the first pulling pulley.

By doing so, the force pulling the anvil becomes greater than the force pushing out the pushing member even in the case in which the same amount of manipulating forces are applied to the first wire and the second wire, and it is possible to stably receive the force from the pushing member with the anvil, and it is possible to perform stable joining by means of the staple.

In addition, the above-described aspect may be provided with an anvil pulling means for pulling the anvil toward the distal end in the longitudinal axial direction with respect to the support member.

By doing so, when clamping the pieces of tissue between the anvil and the pushing member or when releasing the joined pieces of tissue from between the anvil and the pushing member, it is possible to return the anvil to the position that is separated from the pushing member by actuating the anvil pulling means.

In addition, in the above-described aspect, the anvil pulling means may include a third wire that pulls the anvil toward the distal end by being pulled toward the proximal end, the medical manipulator may include an anvil manipulator that includes winding portions around which a proximal end of the third wire and a proximal end of the second wire are individually wound, the anvil manipulator individually applying pulling forces to the second wire and the third wire as a result of rotations of the individual winding portions, and the individual winding portions of the anvil manipulator may be rotated in synchronization at a circumferential speed that is proportional to a ratio of the distances by which the second wire and the third wire are pulled with respect to an amount by which the anvil is moved.

By doing so, the anvil is moved toward the proximal end when the second wire is pulled toward the proximal end by manipulating the anvil-manipulator, whereas the anvil is moved toward the distal end when the third wire is pulled toward the proximal end. In the case in which the pulling force that causes the anvil to be moved toward the proximal end differs from the pulling force that caused the anvil to be moved toward the distal end, the distances by which the second wire and the third wire are pulled with respect to the amount by which the anvil is moved differ from each other. Therefore, as a result of rotating the individual winding portions in synchronization at circumferential speeds where the ratio thereof is equal to the ratio of the distances by which the second wire and the third wire are pulled with respect to the amount by which the anvil is moved, it is possible to enhance the operability by suppressing, when the pulling force is made to act on one of the second wire and the third wire, slackening that occurs in the other wire.

In addition, in the above-described aspect, the anvil manipulator may be formed of a two-stage pulley in which a ratio of diameters of the individual winding portions is equal to the ratio of the distances by which the second wire and the third wire are pulled with respect to the amount by which the anvil is moved, and the second wire and the third wire may be wound therearound in opposite directions.

By doing so, the second wire is pulled when the two-stage pulley constituting the anvil-manipulator is rotated in one direction, and the third wire is pulled when the two-stage pulley is rotated in the other direction. By doing so, it is possible to enhance the operability by suppressing, when the pulling force is made to act on one of the second wire and the third wire, slackening that occurs in the other wire, even if the pulling force that causes the anvil to be moved toward the proximal end differs from the pulling force that causes the anvil to be moved toward the distal end.

In addition, in the above-described aspect, the anvil manipulator may include: two pulleys in which the individual winding portions are provided; and a speed-reducing mechanism that causes the pulleys to be rotated in synchronization at circumferential speeds where a ratio thereof is equal to the ratio of the distances by which the second wire and the third wire are pulled with respect to the amount by which the anvil is moved.

By doing so, as a result of rotating one of the pulleys, the speed-reducing mechanism causes the other pulley to rotate at a different circumferential speed. By doing so, it is possible to enhance the operability by suppressing, when the pulling force is made to act on one of the second wire and the third wire, slackening that occurs in the other wire, even if the pulling force that causes the anvil to be moved toward the proximal end differs from the pulling force that causes the anvil to be moved toward the distal end.

In addition, the above-described aspect may be provided with a pushing-member pulling means for pulling the pushing member toward the proximal end in the longitudinal axial direction with respect to the support member.

In addition, in the above-described aspect, the pushing-member pulling means may include a fourth wire that pulls the pushing member toward the proximal end as a result of being pulled toward the proximal end, the medical manipulator includes a pushing-member manipulator that includes winding portions around which a proximal end of the fourth wire and the proximal end of the first wire are individually wound, the pushing-member manipulator individually applying pulling forces to the first wire and the fourth wire by means of rotations of the individual winding portions, and the individual winding portions of the pushing-member manipulator may be rotated in synchronization at a circumferential speed that is proportional to a ratio of the distances by which the first wire and the fourth wire are pulled with respect to an amount by which the pushing member is moved.

In addition, in the above-described aspect, the pushing-member manipulator may be formed of a two-stage pulley in which a ratio of diameters of the individual winding portions of the pushing-member is equal to the ratio of the distances by which the first wire and the fourth wire are pulled with respect to the amount by which the pushing member is moved, and the first wire and the fourth wire may be wound therearound in opposite directions.

In addition, in the above-described aspect, the pushing-member manipulator may include: two pulleys in which the individual winding portions of the pushing-member manipulator are provided; and a speed-reducing mechanism that causes the pulleys to be rotated in synchronization at circumferential speeds where a ratio thereof is equal to the ratio of the distances by which the first wire and the fourth wire are pulled with respect to the amount by which the pushing member is moved.

REFERENCE SIGNS LIST 1 medical manipulator
2 support member
3 anvil
4 pusher (end effector, pushing member)
6 pusher-driving mechanism (pushing-member pulling means)
7 staple
12 movable pulley (first pulling pulley)
13 pushing wire (first wire)
15 pulling wire (fourth wire)
16b slit
19,20 movable pulley (second pulling pulley)
21, 29 pulling wire (second wire)
22 pushing wire (anvil pulling means, third wire)
24b upper jaw (anvil)
50 manipulating portion (anvil manipulator, pushing-member manipulator)
51 two-stage pulley
51a, 51b, 52a, 52b pulley (winding portion)
53 speed-reducing mechanism
B movable shaft (first shaft)
F, G movable shaft (second shaft)

The invention claimed is:

1. A medical manipulator comprising:
   an elongated support member;
   an end effector that is supported at a distal end of the support member so as to be movable in a longitudinal axial direction, the end effector being a pushing member that pushes out a staple;
   a pusher-driving mechanism configured to move the pushing member;
   an anvil that is supported at the distal end of the support member so as to be movable in the longitudinal axial direction and that deforms the staple that is pushed out by the pushing member toward the distal end in the longitudinal axial direction; and
   an anvil-driving mechanism configured to move the anvil;
   wherein the pusher-driving mechanism comprises:
      a first pulling pulley that is supported so as to be rotatable about a first shaft that is secured to the end effector and that is orthogonal to the longitudinal axis; and
      a first wire that is wound around the first pulling pulley so as to cause, when a proximal end thereof is pulled, tensile forces in substantially the same directions to act on the first pulling pulley on either side of the first pulling pulley flanking the first shaft, and
   wherein the anvil-driving mechanism comprises:
      a second pulling pulley that is supported so as to be rotatable about a second shaft that is secured to the anvil and that is orthogonal to the longitudinal axis; and
      a second wire that is wound around the second pulling pulley so as to cause, when a proximal end thereof is pulled, tensile forces applied toward the proximal end in the longitudinal axial direction on either side of the second pulling pulley flanking the second shaft to act on the second pulling pulley.

2. The medical manipulator according to claim 1, wherein the support member includes a slit that supports an axle of the first pulling pulley so as to allow movement thereof in a longitudinal axial direction.

3. The medical manipulator according to claim 1, wherein two or more sets of the first pulling pulley and the first wire are provided.

4. The medical manipulator according to claim 1, wherein two or more sets of the second pulling pulley and the second wire are provided.

5. The medical manipulator according to claim 1, wherein the number of times the second wire is wound around the second pulling pulley is equal to or greater than the number of times the first wire is wound around the first pulling pulley.

6. The medical manipulator according to claim 1, further comprising:
   an anvil pulling wire that pulls the anvil toward the distal end in the longitudinal axial direction with respect to the support member.

7. The medical manipulator according to claim 6,
   wherein the anvil pulling wire includes a third wire that pulls the anvil toward the distal end by being pulled toward the proximal end,
   the medical manipulator includes an anvil manipulator that includes winding portions around which a proximal end of the third wire and a proximal end of the second wire are individually wound, the anvil manipulator individually applying pulling forces to the second wire and the third wire as a result of rotations of the individual winding portions, and the individual winding portions of the anvil manipulator are rotated in synchronization at a circumferential speed that is proportional to a ratio of the distances by which the second wire and the third wire are pulled with respect to an amount by which the anvil is moved.

8. The medical manipulator according to claim 1, further comprising:

a pushing-member pulling wire that pulls the pushing member toward the proximal end in the longitudinal axial direction with respect to the support member.

9. The medical manipulator according to claim 8, wherein the pushing-member pulling wire includes a fourth wire that pulls the pushing member toward the proximal end as a result of being pulled toward the proximal end, the medical manipulator includes a pushing-member manipulator that includes winding portions around which a proximal end of the fourth wire and the proximal end of the first wire are individually wound, the pushing-member manipulator individually applying pulling forces to the first wire and the fourth wire by means of rotations of the individual winding portions, and the individual winding portions of the pushing-member manipulator are rotated in synchronization at a circumferential speed that is proportional to a ratio of the distances by which the first wire and the fourth wire are pulled with respect to an amount by which the pushing member is moved.

10. The medical manipulator according to claim 9, wherein the pushing-member manipulator is formed of a two-stage pulley in which a ratio of diameters of the individual winding portions of the pushing-member is equal to the ratio of the distances by which the first wire and the fourth wire are pulled with respect to the amount by which the pushing member is moved, and the first wire and the fourth wire are wound therearound in opposite directions.

11. The medical manipulator according to claim 9, wherein the pushing-member manipulator includes:

two pulleys in which the individual winding portions of the pushing-member manipulator are provided; and a speed-reducing mechanism that causes the pulleys to be rotated in synchronization at circumferential speeds where a ratio thereof is equal to the ratio of the distances by which the first wire and the fourth wire are pulled with respect to the amount by which the pushing member is moved.

12. The medical manipulator according to claim 1, wherein a force that causes the anvil to be moved toward the proximal end in the longitudinal axial direction as a result of the second wire being pulled is equal to or greater than a force that causes the pushing member to be moved toward the distal end in the longitudinal axial direction as a result of the first wire being pulled.

13. The medical manipulator according to claim 1, wherein the pusher-driving mechanism is disposed further on a proximal-end side than the pushing member is.

14. A medical manipulator comprising:

an elongated support member;

an end effector that is supported at a distal end of the support member so as to be movable in a longitudinal axial direction, the end effector being a pushing member that pushes out a staple;

a first pulling pulley that is supported so as to be rotatable about a first shaft that is secured to the end effector and that is orthogonal to the longitudinal axis;

a first wire that is wound around the first pulling pulley so as to cause, when a proximal end thereof is pulled, tensile forces in substantially the same directions to act on the first pulling pulley on either side of the first pulling pulley flanking the first shaft;

an anvil that is supported at the distal end of the support member so as to be movable in the longitudinal axial direction and that deforms the staple that is pushed out by the pushing member toward the distal end in the longitudinal axial direction;

a second pulling pulley that is supported so as to be rotatable about a second shaft that is secured to the anvil and that is orthogonal to the longitudinal axis;

a second wire that is wound around the second pulling pulley so as to cause, when a proximal end thereof is pulled, tensile forces applied toward the proximal end in the longitudinal axial direction on either side of the second pulling pulley flanking the second shaft to act on the second pulling pulley;

an anvil pulling wire that includes a third wire that pulls the anvil toward the distal end in the longitudinal axial direction with respect to the support member by being pulled toward the proximal end; and an anvil manipulator that includes winding portions around which a proximal end of the third wire and a proximal end of the second wire are individually wound, the anvil manipulator individually applying pulling forces to the second wire and the third wire as a result of rotations of the individual winding portions, wherein the individual winding portions of the anvil manipulator are rotated in synchronization at a circumferential speed that is proportional to a ratio of the distances by which the second wire and the third wire are pulled with respect to an amount by which the anvil is moved.

15. The medical manipulator according to claim 14, wherein the anvil manipulator is formed of a two-stage pulley in which a ratio of diameters of the individual winding portions is equal to the ratio of the distances by which the second wire and the third wire are pulled with respect to the amount by which the anvil is moved, and the second wire and the third wire are wound therearound in opposite directions.

16. The medical manipulator according to claim 15, wherein the anvil manipulator includes:

two pulleys in which the individual winding portions are provided; and a speed-reducing mechanism that causes the pulleys to be rotated in synchronization at circumferential speeds where a ratio thereof is equal to the ratio of the distances by which the second wire and the third wire are pulled with respect to the amount by which the anvil is moved.

* * * * *